US012582468B2

(12) United States Patent　　　　(10) Patent No.:　US 12,582,468 B2

Laske et al.　　　　　　　　　　　　(45) Date of Patent:　　Mar. 24, 2026

(54) APPLICATION OF NON-THERAPEUTIC WAVEFORMS WITH GRADIENT SENSING TO PREDICT PULSED FIELD ABLATION (PFA) FIELDS

(71) Applicant: Medtronic, Inc., Minneapolis, MN (US)

(72) Inventors: Timothy G. Laske, Shoreview, MN (US); Qingguo Zeng, Solon, OH (US); Qing Lou, Solon, OH (US); Mark T. Stewart, Lino Lakes, MN (US); Brian T. Howard, Minneapolis, MN (US); Anthony W. Rorvick, Champlin, MN (US); Gregory S. Brumfield, Delaware, OH (US)

(73) Assignee: Medtronic, Inc., Minneapolis, MN (US)

( * ) Notice: Subject to any disclaimer, the term of this patent is extended or adjusted under 35 U.S.C. 154(b) by 336 days.

(21) Appl. No.: 18/338,741

(22) Filed: Jun. 21, 2023

(65) Prior Publication Data

US 2023/0414276 A1　　Dec. 28, 2023

Related U.S. Application Data

(60) Provisional application No. 63/354,856, filed on Jun. 23, 2022.

(51) Int. Cl.
　　*A61B 18/14*　　　(2006.01)
　　*A61B 18/00*　　　(2006.01)
(52) U.S. Cl.
　　CPC ..................... *A61B 18/1492* (2013.01); *A61B 2018/00577* (2013.01); *A61B 2018/00702* (2013.01); *A61B 2018/00875* (2013.01)

(58) Field of Classification Search
　　CPC ...... A61B 18/1492; A61B 2018/00577; A61B 2018/00702; A61B 2018/00875;
　　　　　　　(Continued)

(56) References Cited

U.S. PATENT DOCUMENTS 9,113,911 B2　　8/2015　Sherman
11,826,088 B2 *　11/2023　Govari ............... A61B 18/1492
　　　　　　　　(Continued)

FOREIGN PATENT DOCUMENTS

WO　　WO-2017184628 A1 *　10/2017　............. A61B 34/25

OTHER PUBLICATIONS

International Preliminary Report on Patentability for Application No. PCT/US2023/068785 dated Jan. 2, 2025 (9 pages).
(Continued)

*Primary Examiner* — Beverly M Flanagan
(74) *Attorney, Agent, or Firm* — Michael Best & Friedrich LLP

(57)　　　　　　　　ABSTRACT

A method and a pulsed electric field (PEF) ablation instrument are provided. According to one aspect, a method in a PFA generator includes receiving electrical responses for each of at least one non-therapeutic waveform. The process also includes determining an electric field distribution based at least in part on the received electrical responses. The process further includes selecting a non-therapeutic waveform that produces an electric field distribution that satisfies criteria. The process also includes mapping the selected non-therapeutic waveform to an ablative waveform.

16 Claims, 10 Drawing Sheets

(58) Field of Classification Search
CPC ...... A61B 2018/167; A61B 2018/1407; A61B
2018/1435; A61B 2018/00654; A61B
2018/124
USPC ........................................................ 606/34
See application file for complete search history.

(56) References Cited

U.S. PATENT DOCUMENTS

| | | | | |
|---|---|---|---|---|
| 12,114,918 B2 * | 10/2024 | Govari | .................... | A61B 5/287 |
| 12,114,919 B2 * | 10/2024 | Forsyth | .............. | A61B 18/1492 |
| 2016/0143686 A1 * | 5/2016 | Tunay | ................ | A61B 18/1233 |
| | | | | 606/34 |
| 2017/0065339 A1 * | 3/2017 | Mickelsen | ............. | A61N 1/327 |
| 2018/0214202 A1 * | 8/2018 | Howard | .............. | A61B 5/6852 |
| 2022/0047326 A1 * | 2/2022 | Altmann | ................. | A61B 18/12 |
| 2023/0240746 A1 * | 8/2023 | Gundert | ............. | A61B 18/1206 |
| | | | | 606/35 |

OTHER PUBLICATIONS

International Search Report and Written Opinion for Application No. PCT/US2023/068785 dated Oct. 4, 2023 (17 pages).

* cited by examiner

APPLICATION OF NON-THERAPEUTIC WAVEFORMS WITH GRADIENT SENSING TO PREDICT PULSED FIELD ABLATION (PFA) FIELDS

CROSS-REFERENCE TO RELATED APPLICATION

This application claims the benefit of U.S. Provisional Patent Application No. 63/354,856, filed 23 Jun. 2022, and entitled "APPLICATION OF NON-THERAPEUTIC WAVEFORMS WITH GRADIENT SENSING TO PREDICT PULSED FIELD ABLATION (PFA) FIELDS."

FIELD

The present disclosure relates to methods, systems, and devices for enhancing the efficiency and efficacy of ablation energy delivery and improving patient safety.

BACKGROUND

Tissue ablation is used in numerous medical procedures to treat a patient. In some examples, ablation procedures involve modification of target tissue, e.g., to stop electrical propagation through the tissue in patients with an arrhythmia. Such ablation procedures are often performed by passing energy, such as electrical energy, through one or more electrodes of an inserted catheter. The energy causes modifications to the target tissue.

SUMMARY

Pulsed field ablation ("PFA"), which can cause reversible or irreversible electroporation, is a non-thermal ablation technique that creates lesions in desired areas of patient tissue to treat medical conditions, such as cardiac arrhythmias, and to ablate areas of tissues and/or organs in the body. For treating cardiac arrhythmias, for example, PFA can be performed to modify tissue so as to stop aberrant electrical propagation and/or disrupt aberrant electrical conduction through cardiac tissue.

PFA includes application of short pulsed electric fields (PEF), which may reversibly or irreversibly destabilize cell membranes through electro-permeabilization, but generally do not affect the structural integrity of the tissue components, including the acellular cardiac extracellular matrix.

In some PFA systems, the user programs, or otherwise manually enters, the desired parameters of the pulsed electric field to be delivered to the tissue into an electrosurgical generator configured to deliver electrical energy to the target tissue through an electrosurgical hand piece. For a given delivery tool, target tissue, or environment, the user may select from waveform parameters, such as the type, amplitude, shape, frequency, and repetition of the waveform. These parameters affect a size, shape and/or location of the lesion caused by application of the PEF.

The nature of PFA allows for very brief periods of therapeutic energy delivery, on the order of tens of milliseconds in duration. Further, PFA may not cause collateral damage to non-targeted tissue as frequently or severely as thermal ablation techniques. Additionally, pharmacological agents may be preferentially introduced into the cells of targeted tissue that are exposed to PEF having reversible membrane permeabilization.

Catheters inserted and navigated through blood vessels are used to probe and treat a variety of medical conditions.

For example, cardiac arrythmias may be treated by inserting a catheter into a blood vessel and guiding it to the heart. At the end of the catheter are electrodes for applying electrical energy. The electrodes may be used to detect electrical activity in the surrounding tissues and/or to deliver a pulsed electric field to the tissue to disrupt electrical pathways in the tissue to treat the arrythmia. The electrodes may also be used to map the electrical activity in the tissue and then to deliver a PEF signal to cause a pulsed electric field to penetrate into the tissue, thereby hyper-permeabilizing the surrounding cardiomyocytes and disrupting electrical activity in the target tissue.

According to one aspect of this disclosure, a pulsed electric field (PEF) ablation instrument includes processing circuitry configured to deliver a non-therapeutic PEF waveform to a first set of electrodes. The processing circuitry is further configured to determine an electrical response to the delivered non-therapeutic PEF waveform based at least in part on signals received on at least one test electrode. The processing circuitry is also configured to determine an ablative PEF waveform to be applied to a second set of electrodes based at least in part on the electrical response.

According to some aspects, the first set of electrodes and the second set of electrodes have at least one electrode in common. The at least one test electrode on which the signals are received is an electrode of at least one of the first set of electrodes and the second set of electrodes. In some embodiments, the electrical response includes a voltage across a pair of electrodes. In some embodiments, the electrical response includes an electric field gradient that is scaled in the response analyzer or ablative waveform generator by a factor to predict an electric field gradient produced by the ablative PEF waveform. In some embodiments, the electrical response includes an impedance between a pair of electrodes. In some embodiments, the non-therapeutic PEF waveform includes at least one pulse, and the electrical response is determined for each pulse of the at least one pulse. In some embodiments, the ablative PEF waveform includes a second sequence of pulses having the same periodicity as the first sequence of pulses. In some embodiments, the processing circuitry is also configured to display a graphical rendering of the electrical response and a graphical rendering of at least two electrodes selected from at least one of the first set of electrodes, the second set of electrodes, and the at least on test electrode. In some embodiments, the graphical rendering includes a graphical rendering of electric field gradients between pairs of electrodes superimposed on a graphical rendering of an anatomical region to be treated, the electric field gradients being determined from the electrical response to the non-therapeutic PEF waveform.

According to another aspect, a method implemented with a PFA system includes delivering a non-therapeutic PEF waveform to a first set of electrodes. The method also includes determining an electrical response to the delivered non-therapeutic PEF waveform based at least in part on signals received on at least one test electrode. The method also includes selecting a second set of electrodes and determining an ablative PEF waveform to be applied to a second set of electrodes based at least in part on the electrical response.

According to some aspects, the first set of electrodes and the second set of electrodes have at least one electrode in common. In some embodiments, the at least one test electrode on which the signals are received is an electrode of at least one of the first set of electrodes and the second set of electrodes. In some embodiments, the electrical response includes a voltage across a pair of electrodes. In some embodiments, the electrical response an electric field gradient that is scaled in the response analyzer or ablative waveform generator by a factor to predict an electric field gradient produced by the ablative PEF waveform. In some embodiments, the electrical response includes an impedance between a pair of electrodes. In some embodiments, the non-therapeutic PEF waveform includes a first sequence of pulses, and the electrical response is determined for each pulse of the first sequence of pulses. In some embodiments, the ablative PEF waveform includes a second sequence of pulses having the same periodicity as the first sequence of pulses. In some embodiments, the method also includes displaying a graphical rendering of the electrical response and a graphical rendering of at least two electrodes selected from at least one of the first set of electrodes, the second set of electrodes, and the at least on test electrode. In some embodiments, the graphical rendering includes a graphical rendering of electric field gradients between pairs of electrodes superimposed on a graphical rendering of an anatomical region to be treated, the electric field gradients being determined from the electrical response to the non-therapeutic PEF waveform.

According to yet another aspect, a method implemented with a PFA generator includes receiving electrical responses for each of at least one non-therapeutic waveform. The method also includes determining an electric field distribution based at least in part on the received electrical responses. The method further includes selecting a non-therapeutic waveform that produces an electric field distribution that satisfies criteria. The method also includes mapping the selected non-therapeutic waveform to an ablative waveform.

According to some aspects, determining the electrical field distribution includes dividing a voltage across a pair of electrodes by the distance between the pair of electrodes. In some embodiments, selecting the non-therapeutic waveform includes selecting a non-therapeutic waveform that produces a highest ratio of electric field energy within a target region of tissue to electric field energy not within the target region of tissue.

One example provides a medical treatment apparatus. The apparatus includes a plurality of electrodes placeable to be in electrical communication with a targeted site of a patient body. The apparatus also includes a waveform generator configured to selectively apply pulsed electrical waveforms to the plurality of electrodes. The apparatus also includes an electronic controller configured to estimate impedances of electrical paths in the patient body between an anchor electrode and a corresponding set of counter electrodes by causing the waveform generator to apply first waveforms thereto and sensing corresponding electrical currents. The anchor electrode and the corresponding set of counter electrodes are variously selected from the plurality of electrodes. The first waveforms are non-therapeutic waveforms. elec- tronic controller is further configured to select, based on the impedances, a group of electrodes for application of second waveforms to the targeted site. The group of electrodes includes one or more of the variously selected anchor electrodes. The second waveforms are therapeutic wave- forms.

Another example provides a medical treatment method. The method includes, with a waveform generator, selec- tively applying pulsed electrical waveforms to a plurality of electrodes placed to be in electrical communication with a targeted site of a patient body. The method also includes, with an electronic controller, estimating impedances of electrical paths in the patient body between an anchor electrode and a corresponding set of counter electrodes by applying first waveforms thereto and sensing corresponding electrical currents, the anchor electrode and the correspond- ing set of counter electrodes being variously selected from the plurality of electrodes, the first waveforms being non- therapeutic waveforms. The method also includes selecting, with the electronic controller and based on the impedances, a group of electrodes for application of second waveforms to the targeted site, the group of electrodes including one or more of the variously selected anchor electrodes, the second waveforms being therapeutic waveforms.

Yet another example provides a non-transitory computer- readable medium storing instructions that, when executed by an electronic controller of a medical-treatment apparatus, cause the medical-treatment apparatus to perform operations comprising the above medical treatment method.

The details of one or more aspects of the disclosure are set forth in the accompanying drawings and the description below. Other features, objects, and advantages of the tech- niques described in this disclosure will be apparent from the description and drawings, and from the claims.

BRIEF DESCRIPTION OF THE DRAWINGS

A more complete understanding of various embodiments, and the attendant advantages and features thereof, will be more readily apparent from the following detailed descrip- tion when considered in conjunction with the accompanying drawings wherein.

DETAILED DESCRIPTION

Figure 1:
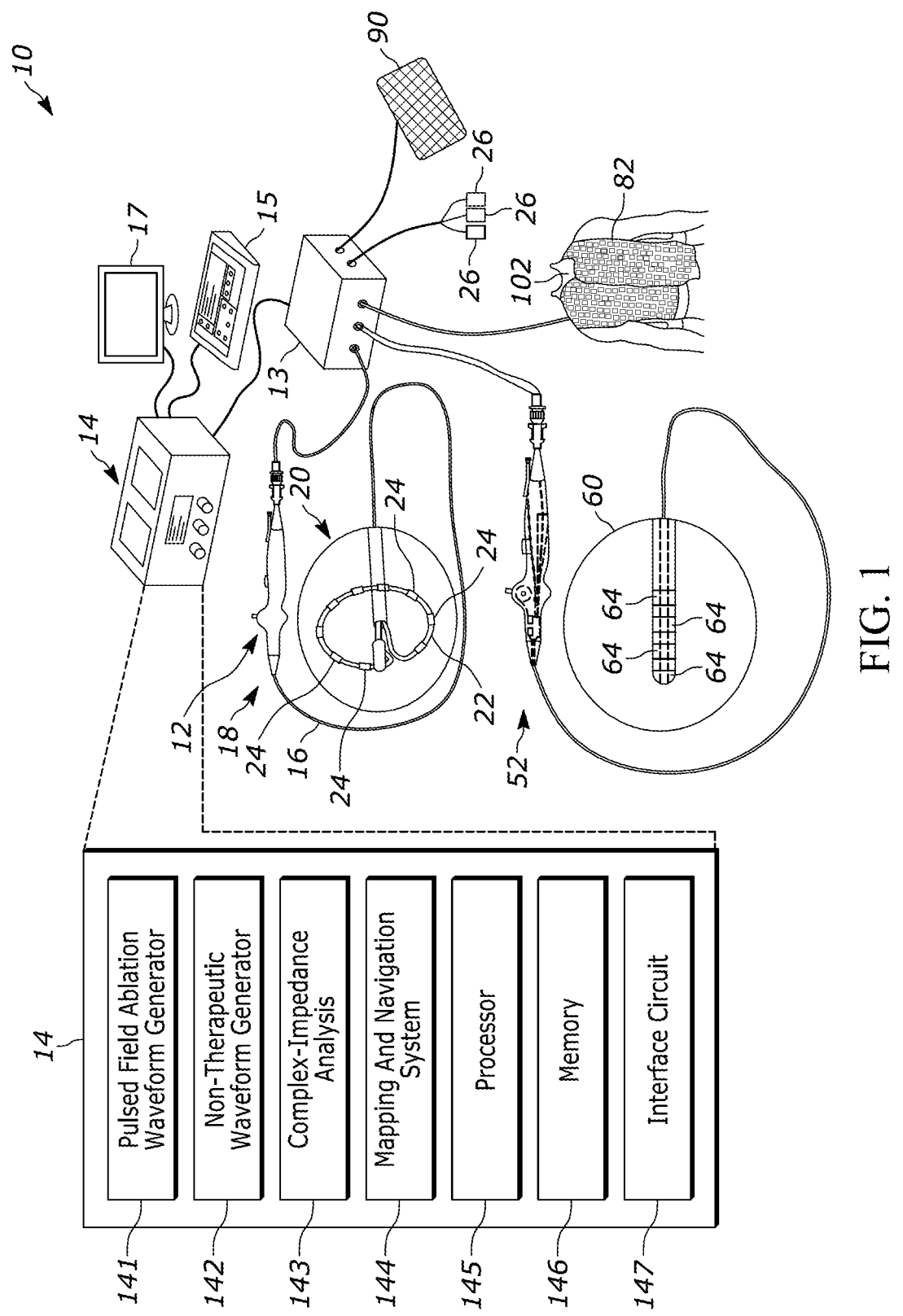
FIG. 1 is a block diagram illustrating a PFA system according to some examples.

Embodiments relate to application of non-therapeutic waveforms with gradient sensing to predict PFA electric fields. According to one aspect, a pulsed electric field (PEF) ablation instrument is configured to deliver a non-therapeu- tic PEF waveform to a first set of electrodes to predict an ablative efficacy of an ablative PEF waveform to be applied to a second set of electrodes. An electrical response to the delivered non-therapeutic PEF waveform is determined. The electrical response is based at least in part on signals received on at least one test electrode. An ablative PEF waveform to be applied to a second set of electrodes is determined based at least in part on the electrical response. This enables the user to predict whether a particular PEF waveform will ablate the target tissue in a desired manner.

Before describing in detail exemplary embodiments, it is noted that the embodiments reside primarily in combinations of apparatus components and processing steps related to application of non-therapeutic waveforms with gradient sensing to predict PFA electric fields. Accordingly, components have been represented where appropriate by conventional symbols in the drawings, showing only those specific details that are pertinent to understanding the embodiments so as not to obscure the disclosure with details that will be readily apparent to those of ordinary skill in the art having the benefit of the description herein. Like numbers refer to like elements throughout the description.

As used herein, the term "pulse" or "pulsed signal" or "pulsed electric field" may include a single pulse, or a train of pulses or multiple trains of pulses. The single pulse, train, or trains of pulses may vary in amplitude, pulse width, and/or other waveform characteristics over a time interval during which the single pulse or pulse train or trains exist(s). The term "non-therapeutic waveform" refers to a waveform that is non-ablative and administered to determine how an area of tissue will respond to an ablative waveform. Non-therapeutic waveforms may include pacing pulses, lower-amplitude PEF waveforms, or any other electrical impulse that can be measured with other electrodes in order to map fields and gradients.

FIG. 1 is a block diagram illustrating one example of a PFA system 10 configured to deliver electrical energy to irreversibly electroporate tissue. In the example shown, the PFA system 10 includes a medical device 12 coupled to an electronic controller 14 configured to provide energy control, delivery, monitoring, and other functions described in more detail below. In various examples, the electrical coupling of the medical device 12 to the electronic controller 14 can be direct (not explicitly shown) or indirect through an electrode connection system (ECS) 13. In the example shown, the electronic controller 14 includes waveform generators 141, 142 configured to generate non-therapeutic PEF waveforms and ablative PEF waveforms.

In various embodiments, the electronic controller 14 has additionally connected thereto, via the ECS 13, one or more of the following components: (i) a medical device 52; (ii) a body surface mapping vest 82; (iii) three or more surface ECG electrodes 26; and (iv) a patient return electrode (PRE) or a large area electrode patch 90. In additional embodiments, the ECS 13 may also provide connections to an additional set of electrodes (not explicitly shown in FIG. 1; e.g., see FIGS. 7-8), for example, including skin surface electrode patches. Some of such electrode patches are used for electric potential navigation of catheters within a patient body 102. In some examples, the skin surface electrode patches include six electrode patches arranged in three pairs, with each of such pairs being aligned along a respective one of the three orientation axes, such as along the Front/Back, Left/Right, and Neck/Leg directions, respectively.

The medical device 12 includes an elongate body 16 passable through the vasculature of the patient body 102 and/or position-able proximate to a tissue region for diagnosis or treatment. In various examples, the elongate body 16 comprises a catheter, sheath, or intravascular introducer. The elongate body 16 has a proximal portion 18 and a distal portion 20 and may include one or more lumens disposed within the elongate body 16 thereby providing mechanical, electrical, and/or fluid communication between the proximal portion 18 of the elongate body 16 and the distal portion 20 of the elongate body 16. The distal portion 20 may generally define the one or more treatment region(s) of the medical device 12 that are operable to monitor, diagnose, and/or treat a portion of the patient body 102.

The treatment region(s) may have a variety of configurations to facilitate such operation. In the case of bipolar pulsed field delivery, a set of electrodes 24 in the distal portion 20 is used in a bipolar configuration for energy delivery where energy passes between one or more electrodes and one or more different electrodes on the same electrode array. In another configuration, one or more of the electrodes 24 serve as one pole while one or more electrodes 64 of the second medical device 52 serve as the opposing pole of the bipolar configuration. For example, as shown in FIG. 1, the distal portion 20 includes an electrode carrier arm 22 that is transition-able between a linear configuration and an expanded configuration in which the carrier arm 22 has an arcuate or substantially circular shape. The electrode carrier arm 22 includes the plurality of electrodes 24 (for example, nine electrodes 24, as shown in FIG. 1) that are configured to deliver pulsed-field energy. Further, the electrode carrier arm 22, when in the expanded configuration, may lie in a plane that is locally substantially orthogonal to the longitudinal axis of the elongate body 16. The planar orientation of the expanded electrode carrier arm 22 may facilitate ease of placement of the plurality of electrodes 24 in contact with the target tissue. The electrodes 64 of the second medical device 52 have a linear configuration as indicated in FIG. 1. For example, a distal portion 60 of the medical device 52 has the electrodes 64 linearly disposed along a common longitudinal axis. In various additional embodiments, other suitable geometric configurations of the electrodes 24, 64 in the medical devices 12, 52 can also be used.

The ECG electrodes 26, when placed on the patient body 102, are used to monitor the patient's cardiac activity. The ECG recordings acquired with the ECG electrodes 26 can be used, e.g., for determining the pulse train delivery timing to coincide with a desired portion of the cardiac cycle, for example, during the ventricular refractory period. The ECG recordings may also be monitored to determine when non-therapeutic stimulation pulses delivered to the myocardium result in activation (capture) of the ventricles.

An input device 15 in communication with the electronic controller 14 is included for operating and controlling various functions of the system 10. The system 10 also includes a display device 17 to display information to the user/operator. The system 10 is further configured to deliver a non-therapeutic PEF waveform using the waveform generator 142 and to determine a response to that waveform. Based on the response to the non-therapeutic PEF waveform, the system 10 operates to determine and then deliver an ablative PEF waveform using the waveform generator 141. These functions enable the user to select an ablative waveform that will more likely produce effective ablation of a target region of tissue without ablating other regions of tissue.

The electronic controller 14 also includes a processor 145 in communication with one or more memories 146 containing software modules providing instructions or algorithms for automated operation and execution of various sequences, calculations, and/or procedures described herein. An interface circuit 147 enables signal transmission and/or communications between various circuits of the electronic controller 14 and other components of the system 10, e.g., as described in more detail below.

The non-therapeutic waveform generator 142 is configured to generate a non-therapeutic waveform to be delivered to the electrodes 24, 64 and/or other pertinent electrodes located in and/or around the region of tissue to be ablated (target tissue). For example, a non-therapeutic waveform may be a train of pulses delivering an electric field having an amplitude of less than a certain threshold value. In various examples, the threshold value represents an electric field amplitude that does not ablate the target tissue. For cardiac tissue, this threshold value may be smaller than approximately 400 volts per centimeter, for example, where a field strength of 400 volts per centimeter is likely to be ablative.

Thus, the electronic controller 14 may deliver an electrical current or pulse to one or more individual electrodes which may include one or more of the electrodes 24, 64 and/or other electrodes mentioned above. Some of the other electrodes may be inserted at a time of performing the methods disclosed herein for determining an ablative PEF waveform that will achieve ablation of the target tissue or may have been inserted at a previous time such as when electrical leads or devices were inserted into the heart to provide pacing signals to control the heart rhythm. For example, the catheters with the electrodes 24, 64 may be inserted to apply either one or both of ablative and non-therapeutic PEF waveforms. Also, some of the electrodes 24, 64 and/or other electrodes may be configured to detect electrical signals in response to the applied non-therapeutic PEF waveforms. Further, electrodes outside the patient may be configured to detect electrical signals in response to the non-therapeutic PEF waveforms applied to one or more of the electrodes 24, 64 within the patient.

In some examples, the electrical signals detected with the various electrodes are analyzed using pertinent circuits (e.g., including a complex-impedance analysis circuit or module) 143 of the electronic controller 14 to determine an ablative PEF waveform to be applied to a set of the electrodes 24 of the medical device 12. For example, in some cases, the electronic controller 14 operates to determine an electric field between a pair of electrodes based on voltages of signals detected between the electrodes of the pair. By determining the electric fields between pairs of electrodes with different orientations with respect to the target tissue, the electronic controller 14 further operates to determine a voltage gradient field in the vicinity of the target tissue. The voltage gradient field may be displayed on the display 17. The magnitude of the voltage at each point in a region of the target tissue may be displayed by a color chosen by a mapping of voltages to colors. These magnitudes, as a function of position, may be overlayed on a map of the region including the target tissue. For example, a graphic image of the human heart and the positions of the various electrodes may be overlayed on the display 17 with the voltage magnitude (as indicated by color and/or intensity) as a function of position within the heart. Alternatively or in addition, the electric field gradient may be displayed by arrows between electrodes. This feature enables the user to try different settings of the applied non-therapeutic waveform to different sets of electrodes to determine a set of electrodes to which an ablative waveform may be applied to best achieve a desired ablation of the target tissue. For example, the user may select a set of electrodes that best concentrates an electric field in the region of the target tissue, while providing a reduced electric field intensity in the region surrounding the target tissue. Note also that impedances between various pairs or sets of electrodes selected from the electrodes 24, 64, the electrodes of the vest 82, and other electrodes can be measured.

In some embodiments, the electronic controller 14 may execute one or more algorithms to determine one or more ablative waveforms and a set of electrodes to which the one or more ablative waveforms are to be applied, based on the analyzed responses, e.g., to achieve an electric field distribution that concentrates the energy of the electric field generated by an ablative waveform to the area of the target tissue. For example, the electronic controller 14 may operate the non-therapeutic waveform generator 142 to generate and deliver a plurality of sets of non-therapeutic waveforms, and the response analyzer 143 then operates to determine, for each set, an electric field distribution between the electrodes. Thereafter, the electronic controller 14 may operate to identify the set of non-therapeutic waveforms that produces the electric field distribution that focusses the energy delivered to the target tissue while minimizing the energy delivered to non-targeted tissue. In some embodiments, the electronic controller 14 multiplies the electric field distribution determined from the electrical responses to the non-therapeutic waveforms by a constant factor to estimate an electric field distribution generated in response to an ablative pulse having an amplitude that is scaled up by the constant factor with respect to the amplitude(s) of the non-therapeutic waveforms.

The ablative waveform generator 141 is configured to generate and deliver an ablative PEF waveform which may be selected based on the electrical responses to non-therapeutic PEF waveforms. In some examples, the ablative waveform generator 141 is operable in one or more modes of operation, including for example: (i) bipolar energy delivery between at least two of the electrodes 24 or other electrically-conductive portions of the medical device 12 within the patient body 102, (ii) monopolar or unipolar energy delivery to one or more of the electrodes 24 or electrically-conductive portions on the medical device 12 within the patient body 102 and through either one or more of the electrodes 64 of the second medical device 52 within the patient body 102 or the patient return or ground electrode 90 spaced apart from the plurality of electrodes 24 of the medical device 12, such as on the patient's skin or on an auxiliary device positioned away from the medical device 12, and (iii) a combination of the monopolar and bipolar modes.

In addition to monitoring, recording or otherwise conveying measurements or conditions within the medical device 12 or the ambient environment at the distal portion of the medical device 12, additional measurements may be made through connections to the multi-electrode catheter including, for example, temperature, electrode-tissue interface impedance, delivered charge, current, power, voltage, work, or the like in the electronic controller 14 and/or the medical device 12. The surface ECG electrodes 26 may be in communication with the electronic controller 14 for initiating or triggering one or more alerts or therapeutic deliveries during operation of the medical device 12. Additional neutral electrode patient ground patches (not pictured in FIG. 1; see FIGS. 7-8) may be employed to evaluate the desired bipolar electrical path impedance, as well as monitor and alert the operator upon detection of inappropriate and/or unsafe conditions, which include, for example, improper (either excessive or inadequate) delivery of charge, current, power, voltage, and work performed by the plurality of electrodes 24; improper and/or excessive temperatures of the plurality of electrodes 24, improper electrode-tissue interface impedances, and improper and/or inadvertent electrical connections to the patient body 102 prior to delivery of high voltage energy.

The electronic controller 14 further includes a mapping and navigation system 144, either integrated therein or as a physically separate subsystem, configured to track and monitor the positions of the plurality of the electrodes 24 and/or 64 as the medical devices 12, 52 move within the patient body 102. The communication or conveyance of information from the electrodes 24, 64 and the body surface mapping vest 82 to the mapping and navigation system 144 occurs via the ECS 13. In operation, the electronic controller 14 makes use of the connection to the delivery catheter 16 to gather additional information, e.g., for assessing cardiac cycle information for display and/or gating of the geometry. In some examples, the catheter 52 also communicates with the mapping and navigation system 144. The mapping and navigation system 144 may cooperate with other circuitry of the electronic controller 14 to measure a position of at least one of the electrodes 24, 64 prior to, during, and/or after generation and delivery of waveforms. The mapping and navigation system 144 can be used to navigate to various energy delivery points and evaluate an electric field distribution to estimate at least one metric of a therapeutic effect from the PEF delivery at various positions.

Figures 2, 3:
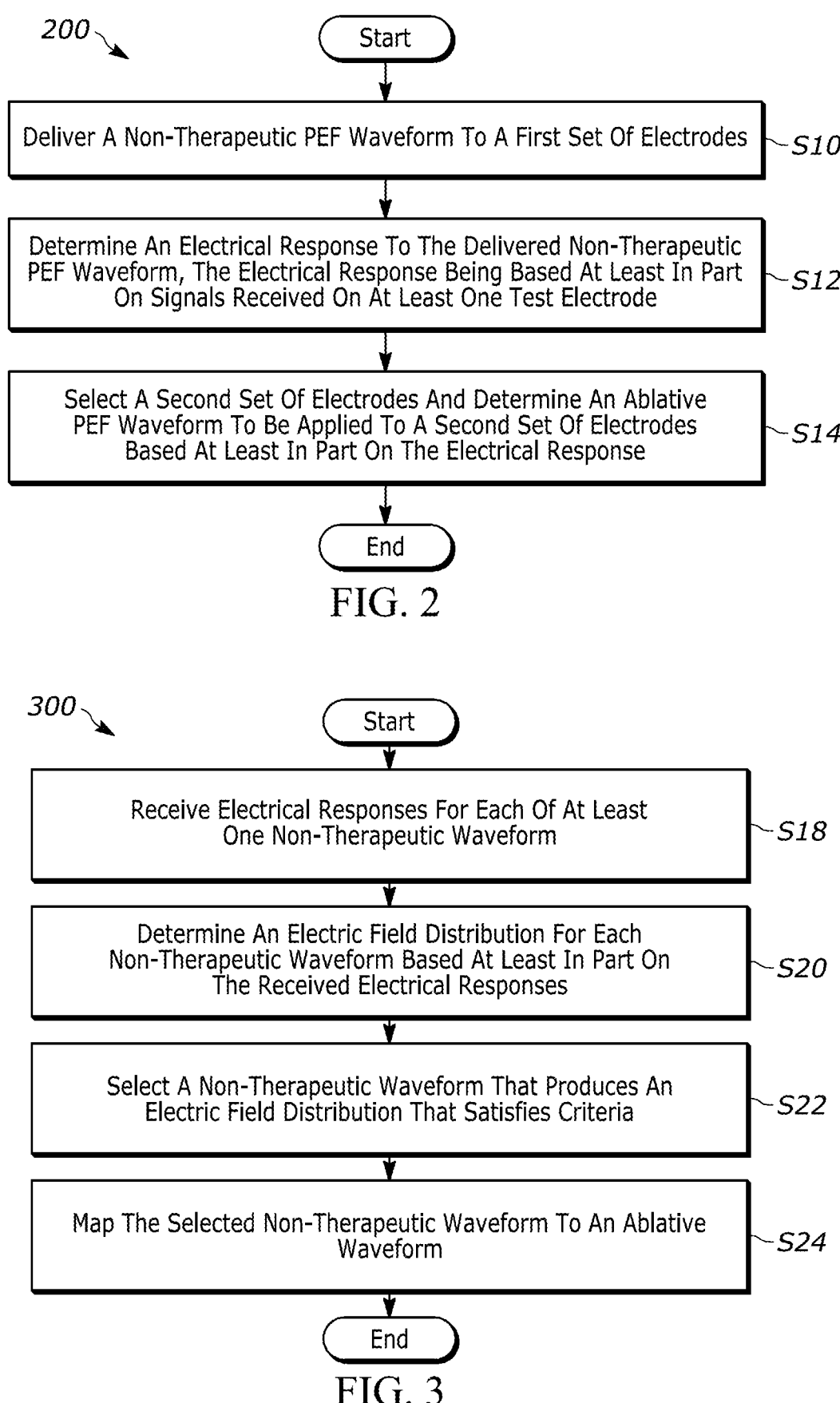
FIG. 2 is a flowchart illustrating a method implemented in the PFA system of FIG. 1 according to some examples.
FIG. 3 is a flowchart illustrating a method implemented in the PFA system of FIG. 1 according to additional examples.

FIG. 2 is a flowchart illustrating a method 200 implemented in the system 10 according to some examples. The method 200 includes delivering a non-therapeutic PEF waveform to a first set of electrodes (in Block S10). The method 200 also includes determining an electrical response to the delivered non-therapeutic PEF waveform based at least in part on signals received on at least one test electrode (in Block S12). The method 200 further includes selecting a second set of electrodes and determining an ablative PEF waveform to be applied to the second set of electrodes based at least in part on the electrical response (in Block S14).

In some examples, the first set of electrodes and the second set of electrodes are selected from the electrodes 24, 64 and have at least one electrode in common. In some examples, the at least one test electrode on which the signals are received is an electrode of at least one of the first set of electrodes 24, 64 and the second set of electrodes 24, 64. In some embodiments, the electrical response includes a voltage across a pair of electrodes 24 and/or 64. In some examples, the sets of electrodes to which a non-therapeutic pulse is applied, the set of electrodes by which a response is measured, and the set of electrodes to which an ablative pulse is applied are selected by the user. In some examples, the electrical response includes an electric field gradient that is scaled in the electronic controller 14 by a selected or fixed factor to estimate an electric field gradient produced by the ablative PEF waveform. In some examples, the electrical response includes an impedance between a pair of electrodes 24 and/or 64. In some examples, a non-therapeutic PEF waveform includes at least one pulse, and the electrical response is determined for each pulse of the at least one pulse. In some examples, the ablative PEF waveform includes a second sequence of pulses having the same periodicity as the first sequence of pulses including the at least one pulse. In some examples, the method 200 also includes displaying a graphical rendering of the electrical response and a graphical rendering of at least two electrodes selected from at least one of the first set of electrodes, the second set of electrodes, and the at least one test electrode. In some examples, the graphical rendering includes a graphical rendering of electric field gradients between the pairs of electrodes superimposed on a graphical rendering of an anatomical region to be treated, the electric field gradients being determined from the electrical response to the non-therapeutic PEF waveform.

FIG. 3 is a flowchart illustrating a method 300 implemented in the system 10 according to further examples. In some examples, the method 300 is used for determining an ablative waveform based on an analysis of electrical responses to non-therapeutic waveforms. The method 300 may be performed using various circuits of the electronic controller 14. The method 300 includes receiving electrical responses for one or more non-therapeutic waveforms (in Block S18). The method 300 also includes determining an electric field distribution based at least in part on the received electrical responses (in Block S20). In some examples, operations of the Block S20 include computing an electric field distribution between each of at least one pair of electrodes by dividing a voltage between the pair of electrodes by the distance between the electrodes of the pair. The method 300 further includes selecting a non-therapeutic waveform that produces an electric field distribution that satisfies applicable criteria (in Block S22). For example, the processor 145 may select the non-therapeutic waveform from the set of previously applied non-therapeutic waveforms) that produces an electric field distribution that approximately maximizes the electric field magnitude in the target tissue while approximately minimizing the electric field magnitude in non-targeted tissue. The method 300 also includes mapping the selected non-therapeutic waveform to an ablative waveform (in Block S24). In some examples, the mapping operations of the Block S24 include applying a respective scaling factor to each of one or more parameters of the selected non-therapeutic waveform to determine the corresponding parameters of the ablative waveform.

In some examples, determining the electrical field distribution in the Block S20 includes dividing a voltage between a pair of electrodes by the distance between the pair of electrodes. In some examples, selecting the non-therapeutic waveform in the Block S22 includes selecting a non-therapeutic waveform that produces an approximately highest ratio of the electric field energy within a target region of tissue to the electric field energy outside the target region.

Figure 4:
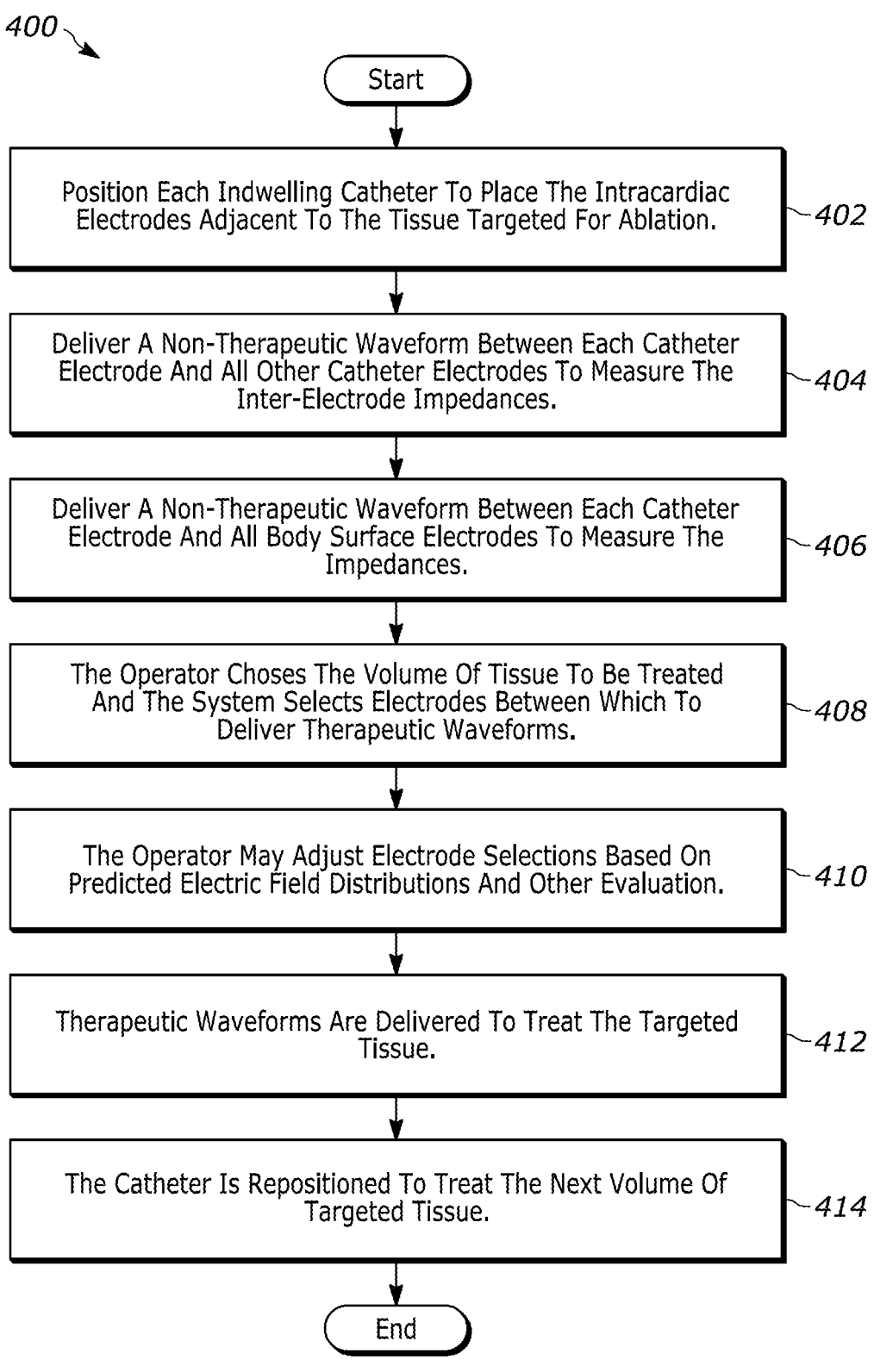
FIG. 4 is a flowchart illustrating a method implemented in the system of FIG. 1 according to further examples.

FIG. 4 is a flowchart illustrating a method 400 implemented in the system 10 according to additional examples. The method 400 uses the mapping and navigation system 144 for rendering the organs adjacent to the pertinent electrodes (e.g., subsets of the electrodes 24, 64) and tissues to be targeted for therapy. In one example, the mapping and navigation system 144 operates to provide a graphic image of the patient's heart on the display 17 and overlays thereon the positions of the pertinent electrodes. This feature enables the operator of the system 10 to visualize where the electrodes 24, 64 are positioned with respect to the targeted tissues. Upon delivering the non-therapeutic waveforms to the targeted tissues via the pertinent electrodes, the electronic controller 14 operates to add to the graphic image the estimated electric field distributions within the targeted and adjacent tissues for different electrode selections. The combined information visualized on the display 17 can then be beneficially used by the operator to target the selected tissue volume more precisely for an intended therapeutic effect. In various embodiments of the method 400, the electrode selection can be fully automated, semi-automated, or performed manually by the operator. In each of such embodiments, groups of electrodes can be selected to obtain an electric field distribution that is approximately optimal for treating the target tissue towards the intended therapeutic effect. In some examples, interelectrode non-therapeutic pulse deliveries to sequential electrode selections are performed at a relatively high frequency, e.g., to enable the selection cycle-through to be completed in less than about 200 milliseconds.

The method 400 includes positioning the distal catheter portions 20, 40 such that the electrodes 24, 64 are placed adjacent or relatively close to the tissue targeted for ablation (in a block 402). In various examples, the positioning operations of the block 402 are aided by the above-described graphic images produced with the mapping and navigation system 144 and displayed on the display 17.

The method 400 also includes measuring the catheter inter-electrode impedances (in a block 404). In some examples, operations of the block 404 include delivering one or more non-therapeutic waveforms between a selected one of the electrodes 24, 64 (referred to as the anchor electrode) and other catheter electrodes and sensing the corresponding voltages and currents between the corresponding electrode pairs. The selection of the anchor electrodes 24, 64 is changed to cycle the selections through all possible combinations of the electrodes 24, 64. The corresponding values of the voltages and sensed currents are then processed, e.g., in the response analyzer 143, to determine the corresponding (typically complex valued) inter-electrode impedances.

The method 400 further includes measuring the catheter-to-surface inter-electrode impedances (in a block 406). In some examples, operations of the block 406 include delivering one or more non-therapeutic waveforms between a selected anchor electrode 24 or 64 and surface electrodes positioned on the skin of the patient's body 102 and sensing the corresponding currents between electrode pairs. The anchor electrode is changed to cycle the selections through all possible combinations of the electrodes 24 and surface electrodes. The values of the sensed voltages and currents are then processed, e.g., in the response analyzer 143, to determine the corresponding complex inter-electrode impedances.

The method 400 also includes selecting electrodes between which to deliver therapeutic waveforms (in a block 408). In one example, operations of the block 408 include receiving an input from the operator regarding the volume of tissue to be treated, e.g., using a user interface and with the aid of the information visualized on the display 17 as indicated above. The operator may also input or select the pertinent parameters for the intended therapeutic effect (in the block 408). The processor 145 then processes the received operator input using the various impedances measured in the blocks 404, 406 to identify a proposed selection of electrodes for the delivery of therapeutic waveforms.

The method 400 also includes receiving additional input from the operator (in a block 410). The additional input received in the block 410 is in response to the automated electrode selection made in the block 408 and is directed at making adjustments to such electrode selection based on auxiliary information (when pertinent and/or available). In some examples, the adjustments are based on predicted or estimated electric field distributions, dynamic stability evaluation, and/or additional patient-specific considerations. In some examples, the operator may reposition the catheter and repeat at least some of the measurements using non-therapeutic waveforms. In some examples, operations of the block 410 are optional and may be omitted.

The method 400 also includes delivering therapeutic waveforms to treat the targeted tissue (in a block 412). The therapeutic waveforms are delivered using the electrode selection of the block 408 optionally adjusted in the block 410. Upon completion of the delivery and evaluation of the treatment results in the block 412, the catheter(s) may optionally be repositioned in a block 414 in preparation for the next round of PEF energy delivery.

Figure 5A:
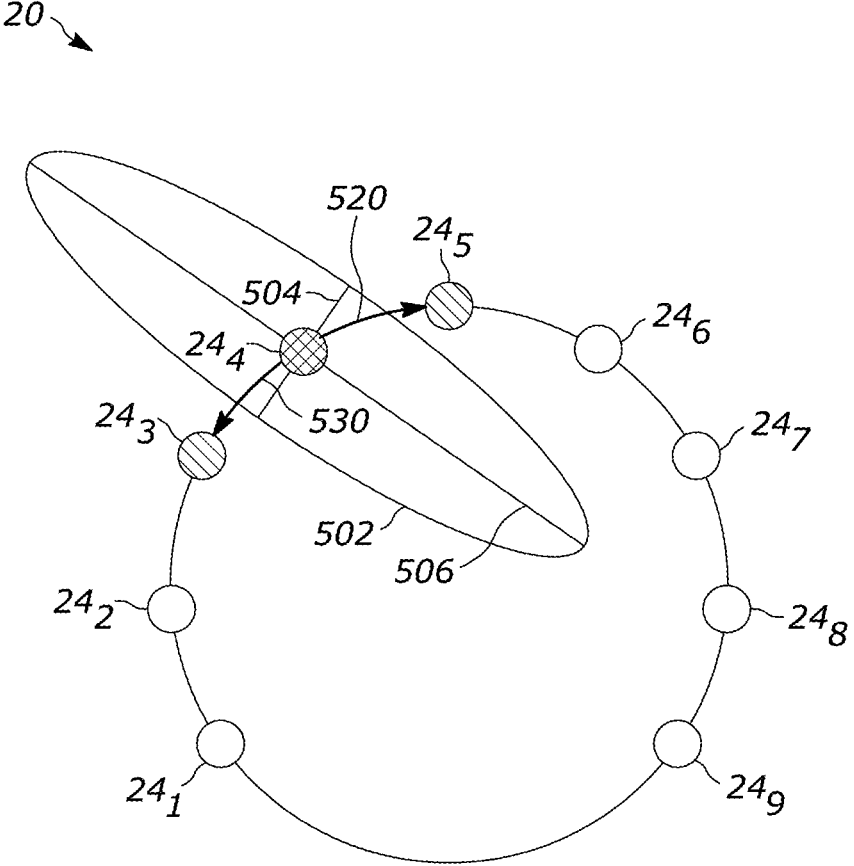
FIGS. 5A-5B are illustrations of electrical gradients between electrodes relative to an area of tissue according to some examples.
Figure 5B:
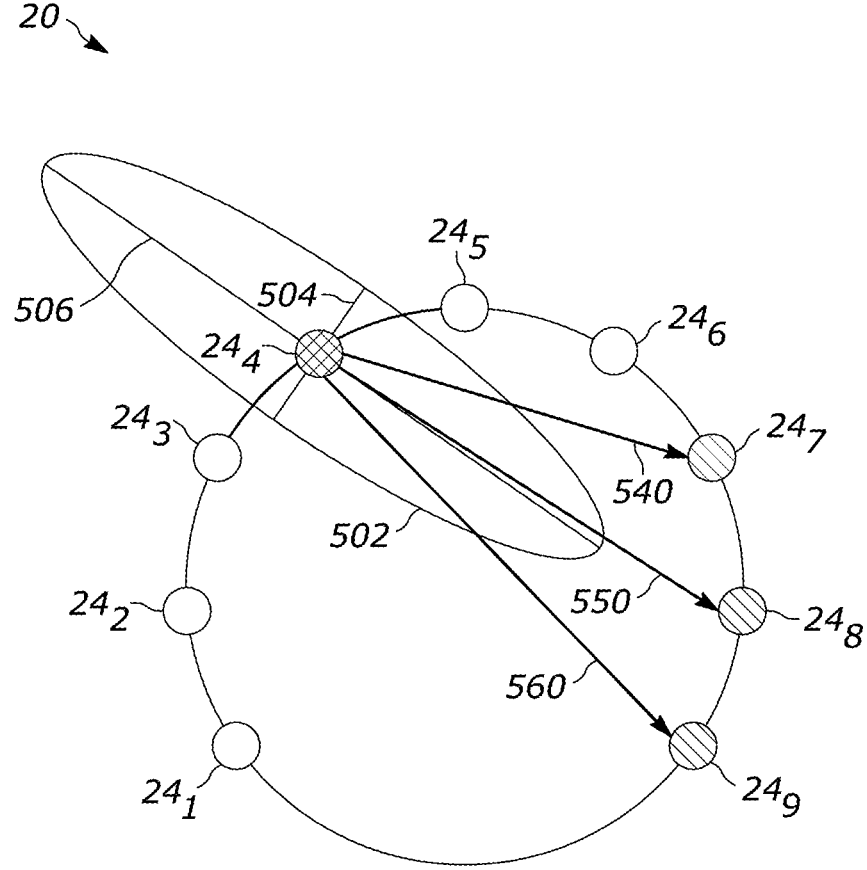

FIGS. 5A-5B are illustrations of electrical gradients between different pairs of the electrodes 24 relative to a targeted area 502 of tissue according to some examples. The targeted area 502 is illustratively shown as having an approximately oval shape. The short and long axes of the oval shape are labeled 504 and 506, respectively. The distal portion 20 of the catheter 12 is positioned, via operations of the block 402 of the method 400, such that the electrode $24_4$ thereof is approximately centered with respect to the targeted area 502. Different electrode selections then enable the electric field vectors to be variously oriented with respect to the axes 504 and 506 as explained in more detail below.

FIG. 5A is an illustration of the electrode selections in which electrical field vectors 520 and 530 are approximately aligned with the short axis 504. The corresponding pairs of electrodes are $(24_3, 24_4)$ and $(24_4, 24_5)$. In some examples, the shown electrode selections cause the corresponding electric fields to align substantially along a minimum impedance axis of the area 502.

FIG. 5B is an illustration of the electrode selections in which electrical field vectors 540, 550, and 560 are approximately aligned with the long axis 506. The corresponding pairs of electrodes are $(24_4, 24_7)$, $(24_4, 24_8)$, and $(24_4, 24_9)$. Although FIGS. 5A and 5B show planar views, a person of ordinary skill in the pertinent art will readily understand that the illustrated concepts are similarly applicable in three dimensions, such as for a spherical volume, a spheroid, or more complex geometries and impedance axes (or other measurable electrical quantity), depending on the available vectoring geometries evaluated with non-therapeutic pulses at the block 406 of the method 400.

Figure 6:
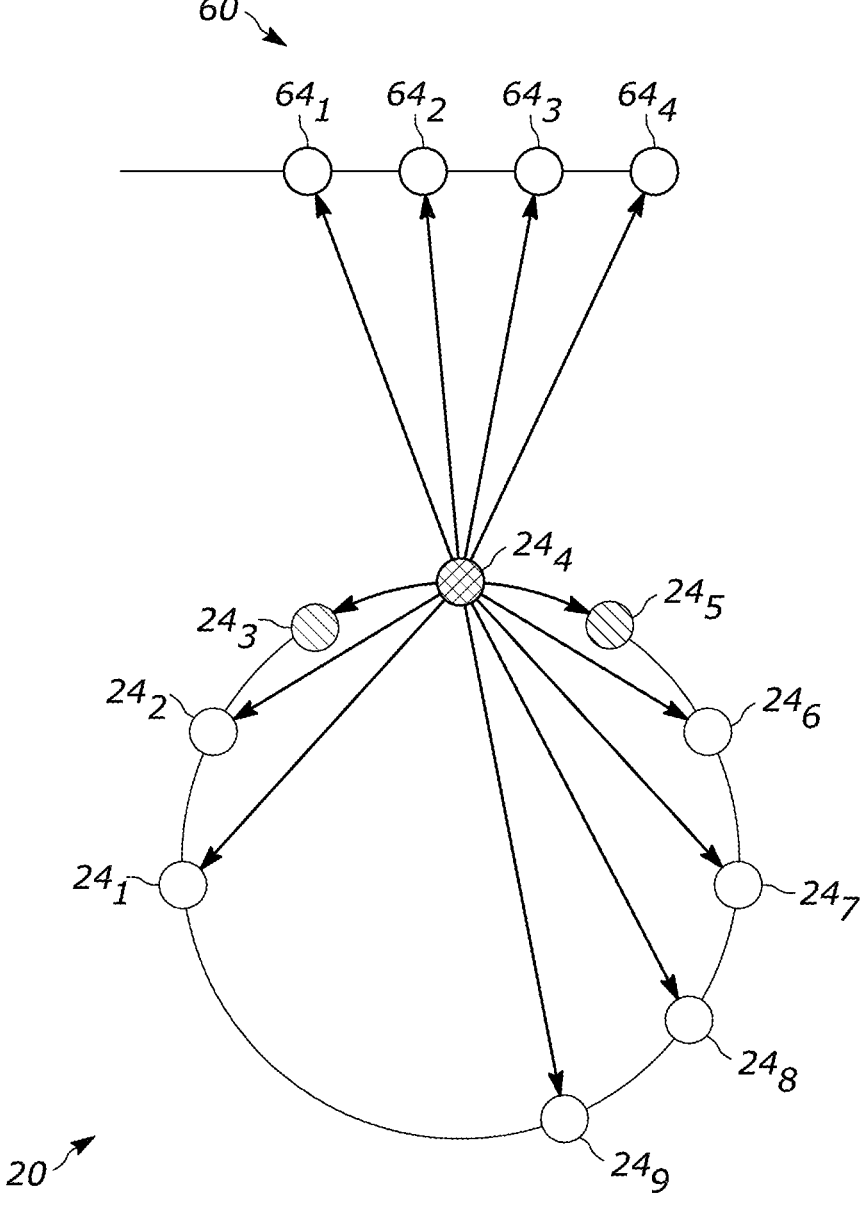
FIG. 6 is a block diagram illustrating impedance vector- ing operations of the method of FIG. 4 according to one example.

FIG. 6 is a block diagram illustrating impedance vectoring operations of the block 404 of the method 400 according to one example. In the example shown, the electrode $24_4$ in the distal portion 20 of the catheter 12 is selected as an anchor electrode of the impedance vectoring. The electrodes $24_1$-$24_3$ and $24_5$-$29_3$ of the distal portion 20 of the catheter 12 and the electrodes $64_1$-$64_4$ of the distal portion 60 of the catheter 52 are sequentially selected to serve as counter electrodes to the anchor electrode $24_4$. For each such sequential selection, a non-therapeutic waveform is transmitted between the anchor electrode $24_4$ and the selected counter electrode, as indicated in FIG. 6 by the different vector arrows. The values of the applied voltages and sensed currents for each selection are then processed in the block 404 of the method 400 to determine the corresponding inter-electrode impedances. The block 404 of the method 400 typically includes sequentially selecting each of the electrodes $24_1$-$24_9$ as the anchor electrode and performing the impedance vectoring similar to that indicated in FIG. 6 for each anchor-electrode selection.

Figure 7:
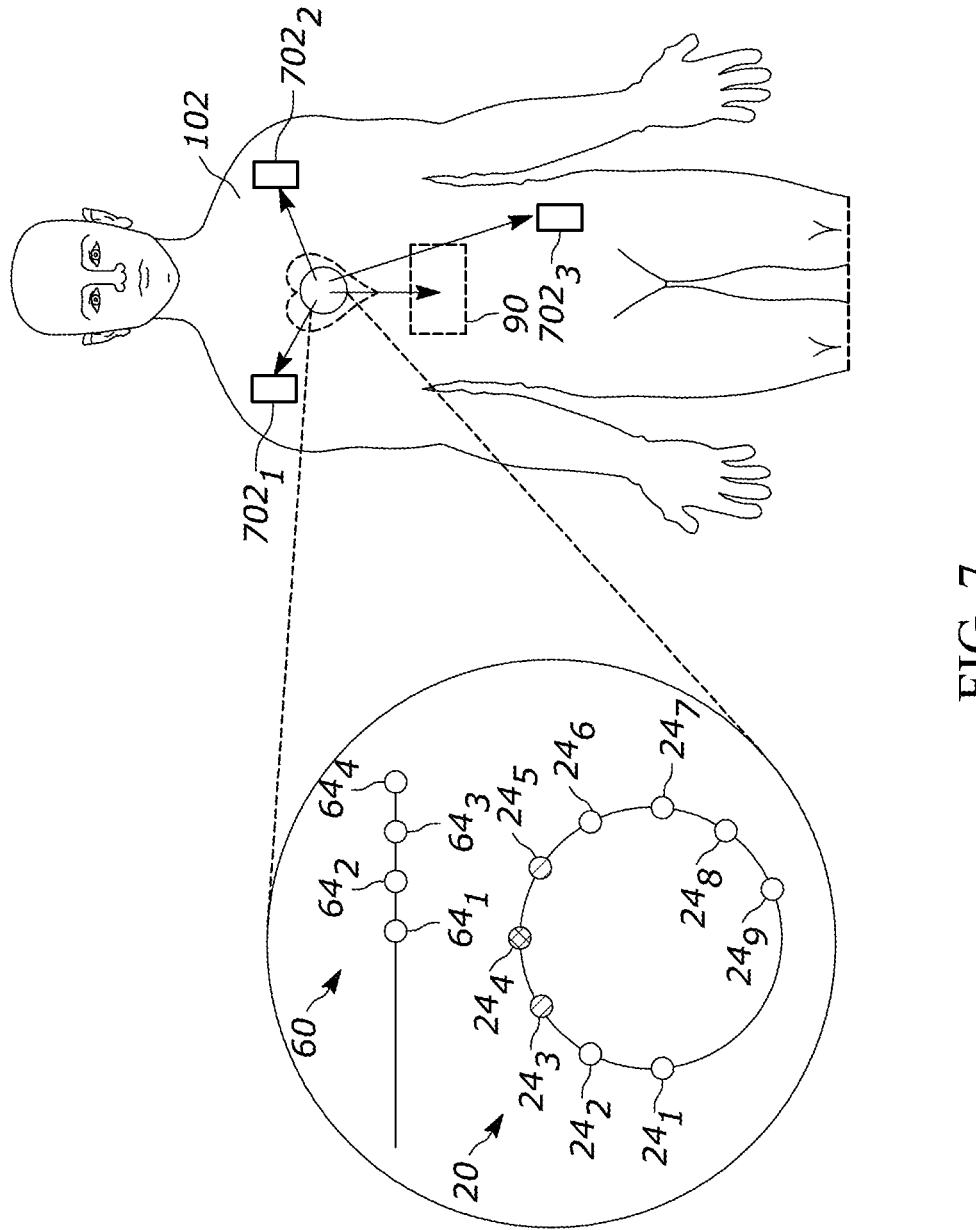
FIG. 7 is a block diagram illustrating impedance vector- ing operations of the method of FIG. 4 according to another example.

FIG. 7 is a block diagram illustrating impedance vectoring operations of the block 406 of the method 400 according to one example. In the example shown, the surface electrodes (patches) include the PRE 90 and surface electrodes $702_1$, $702_2$, and $702_3$. The PRE 90 is positioned at the lower back of the patient body 102. The surface electrodes $702_1$, $702_2$, and $702_3$ are positioned at the right shoulder, left shoulder, and left hip, respectively, of the patient body 102. In other examples, other positions of the surface electrodes can similarly be used. The catheter configuration illustrated in the circular expansion panel in FIG. 7 is the same as that shown in FIG. 6.

In the example shown in FIG. 7, the impedance vectoring operations of the block 406 of the method 400 include sequentially selecting each of the electrodes 24$_1$-24$_9$ and 64$_1$-64$_4$ as the anchor electrode. For each of such sequential selections, the surface electrodes 90, 702$_1$, 702$_2$, and 702$_3$ are sequentially selected to serve as counter electrodes to the selected anchor electrode. A non-therapeutic waveform is transmitted between the anchor electrode and the selected counter electrode, as simplistically indicated in FIG. 7 by the different vector arrows. The values of the applied voltages and sensed currents for each selection are then processed in the block 406 of the method 400 to determine the corresponding inter-electrode impedances.

Figure 8A:
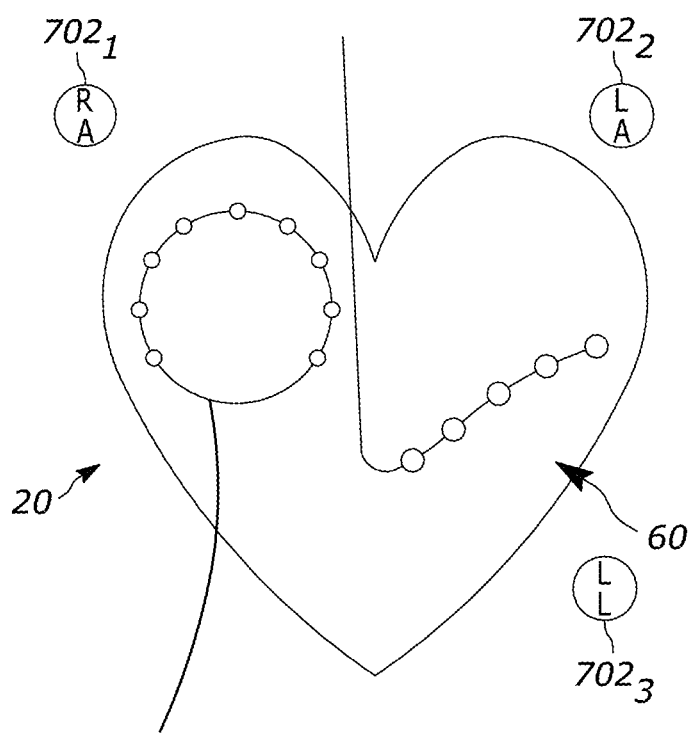
FIGS. 8A-8D are block diagrams illustrating certain operations of the method of FIG. 4 according to some additional examples.

FIGS. 8A-8D are block diagrams illustrating certain operations of the method 400 according to some examples. FIG. 8A illustrates the overall electrode configuration of the system 10 in which the method 400 is performed in this case. The electrode configuration of FIG. 8A is generally similar to that shown in FIG. 7 except that the distal portion 60 of the catheter 52 has five electrodes 64 rather than four.

Figure 8B:
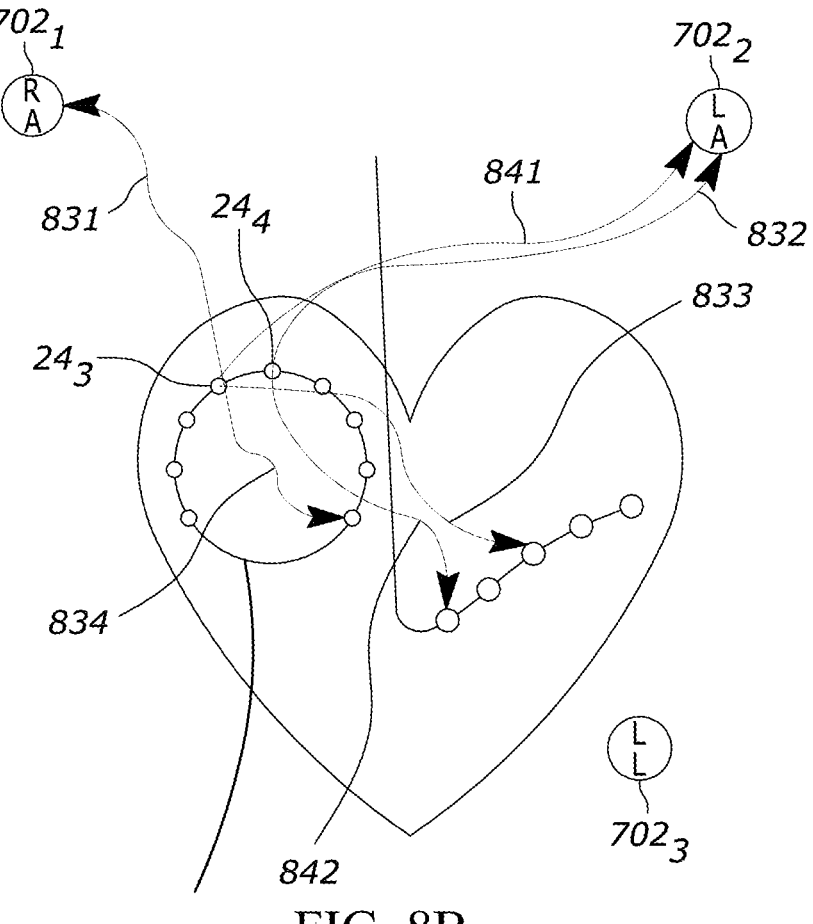

FIG. 8B illustrates example signal pathways along which non-therapeutic waveforms propagate through the patient body 102 during a subset of impedance vectoring operations of the blocks 404, 406 of the method 400. Two sets of such signal pathways are shown in FIG. 8B. The first set of signal pathways represents several impedance vectoring configurations in which the electrode 24$_3$ is the anchor electrode. The corresponding example pathways are labeled 831-834. The second set of signal pathways represents several impedance vectoring configurations in which the electrode 24$_4$ is the anchor electrode. The corresponding example pathways are labeled 841 and 842. Some of the pathways 831-834, 841, and 842 are between the distal portions 20 and 60. Some other of the pathways 831-834, 841, and 842 are between the distal portion 20 and the surface electrodes 702$_1$, 702$_2$.

Figure 8C:
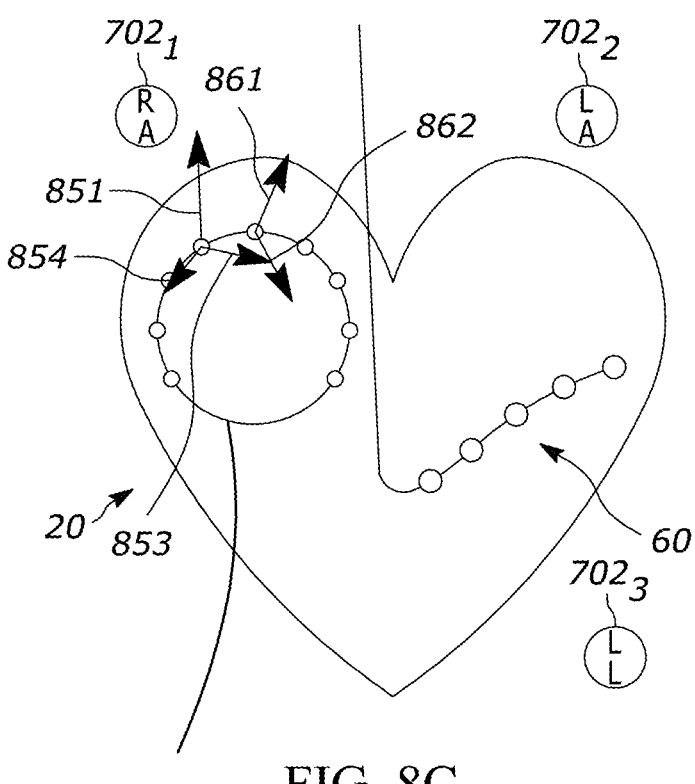

FIG. 8C illustrates an example vectoring configuration selected in the blocks 408, 410 of the method 400 for delivery of therapeutic waveforms. In the example shown, the selected vectoring configuration has five vectors, which are labeled 851, 853, 854, 861, and 862. The selection is based on evaluation of the pathways 831-834, 841, and 842 shown in FIG. 8B and of other signal pathways (not explicitly shown) that have been cycled through in the blocks 404, 406 of the method 400. Based on such evaluation, five electrode pairs corresponding to the signal pathways 831, 833, 834, 841, and 842 have been selected for delivery of therapeutic waveforms. The vectors 851, 853, 854, 861, and 862 represent the delivery of such therapeutic waveforms via those five electrode pairs.

Figure 8D:
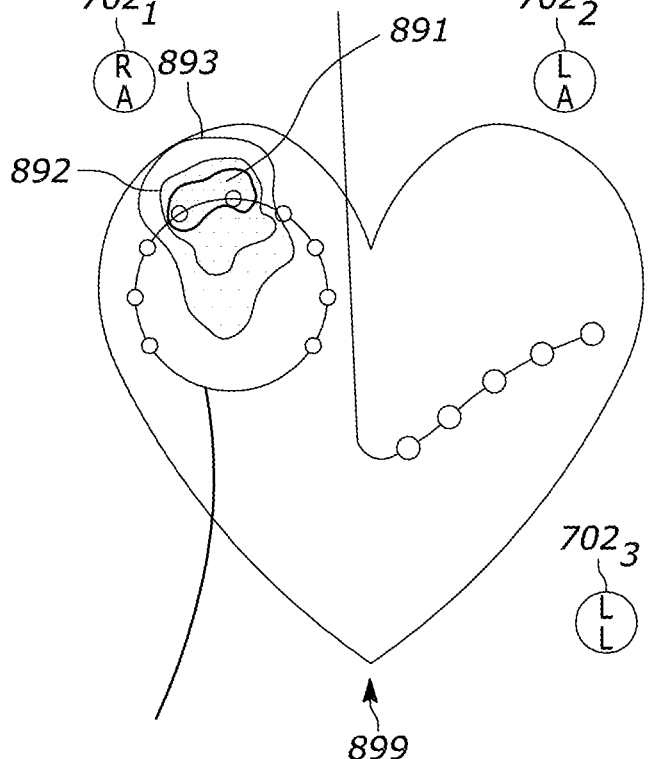

FIG. 8D illustrates an example graphic image 899 of the estimated PEF effects within the targeted and adjacent tissues for the therapeutic vectoring configuration illustrated in FIG. 8C. The graphic image 899 may be displayed on the display 17, e.g., in the block 408 or 410 of the method 400. For illustration purposes and without any implied limitations, the graphic image 899 is shown in FIG. 8D as displaying three different zones of estimated PEF effects: a thermal zone 891, an ablation zone 892, and a reversible electroporation zone 893. In other examples, a different (from three) number of zones can similarly be delineated and displayed.

In some examples, one or more of the following selection criteria and/or considerations are applied to the selection of electrode pairs for therapeutic delivery based on the impedance vectoring measurements, such as the electrode pairs selected for the vectoring configuration illustrated in FIG. 8C:

(1) For single catheter measurements, the individual electrode impedance measurements enable selection of the electrode pairs needed to apply therapeutic electric fields on the targeted tissue volume.

(2) For multi-catheter measurements, the impedances may be used to estimate or predict the tissue volume which the therapeutic field will encompass. Different electrode pairs may be selected or deselected on each of the multiple catheters for therapeutic delivery to obtain the desired PEF exposure in the targeted tissue volume.

(3) Measurement results can indicate when some electrodes are unacceptably close to each other. The electrodes identified in this manner can be deselected to avoid electrical short circuits or overcurrent situations. Unacceptably close proximity of two electrodes may be indicated by the low impedance value directly measured between those electrodes or alternatively inferred from the impedance field calculated from impedance measurements on a plurality of other electrodes.

(4) In some cases, measurement results may provide an indication of previously ablated tissues, based on observation of lower-than-normal impedances in some areas of tissue. Such an indication may then be used, e.g., to adjust the catheter positioning and/or to deselect poles within the ablated region, e.g., by turning OFF the corresponding electrodes, to drive current concentrations to the areas that have not been assessed by the measurements to have impedance values indicating previous effective ablation.

Figure 9:
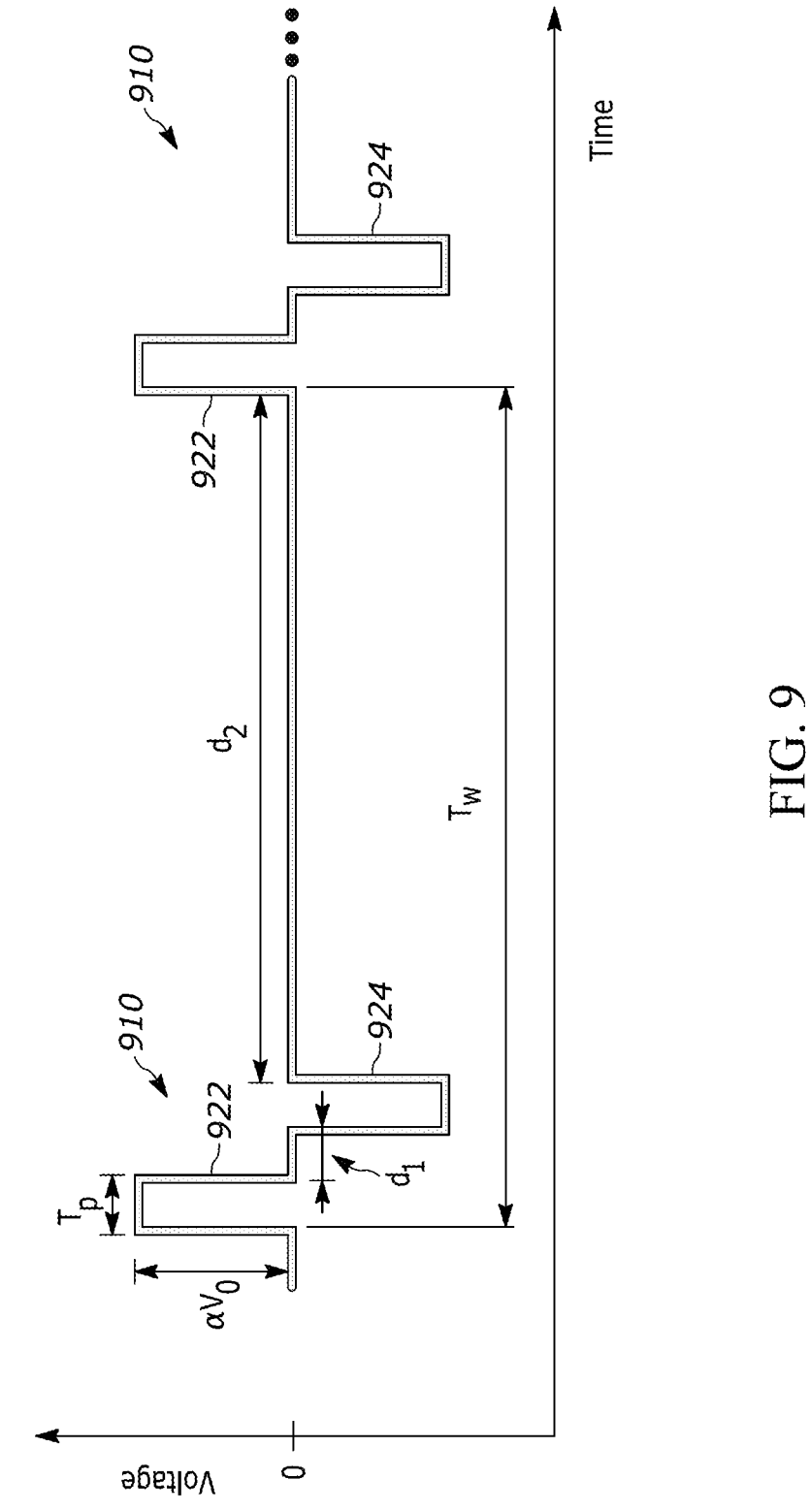
FIG. 9 graphically illustrates an electrical waveform that can be used in the method of FIG. 4 according to some examples.

FIG. 9 graphically illustrates an electrical waveform 902 that can be used in the method 400 according to some examples. The electrical waveform 902 includes a sequence of biphasic pulses 910, each including a respective positive pulse 922 and a respective negative pulse 924. In the example shown, each pulse 922, 924 has an absolute amplitude value $\alpha V_0$ and a pulse width $T_p$, where $V_0$ is a constant. Both the scaling factor $\alpha$ and the pulse width $T_p$ are selectable and controllable via the electronic controller 14. For example, a relatively large value of $\alpha$ may be used to obtain a therapeutic waveform 902 whereas a relatively small value of $\alpha$ may be used to obtain a non-therapeutic waveform 902. The time delay between the positive pulse 922 and the negative pulse 924 of the same biphasic pulse 910 is $d_1$. The parameter $d_1$ is often referred to as the interphase delay. The time delay between two consecutive biphasic pulses 910 in the waveform 902 is $d_2$. The parameter $d_2$ is often referred to as the inter-pulse delay. The waveform 902 has a period $T_w = d_1 + d_2 + 2T_p$. In some examples, the period $T_w$ is in the range between 0.1 ms and 10 ms. In general, the waveform 902 has N biphasic pulses 910, where N is a positive integer. The parameters N, $d_1$, $d_2$, and $T_w$ of the waveform 902 are also selectable and controllable via the electronic controller 14.

In some examples, one or more of the following considerations are applied when configuring the ablative waveform generator 141 for delivery of therapeutic waveforms:

(i) Biphasic waveforms, such as the waveform 902, are characterized by an approximately zero net charge applied to the targeted tissue, which is beneficial for many treatment scenarios.

(ii) The value of $\alpha V_0$ is selected to produce an electric field strength greater than approximately 350 V/cm in the vicinity of the corresponding electrodes. This electric field strength corresponds to the irreversible electroporation threshold of a specific targeted tissue, in this example, cardiac myocytes. The value of $\alpha V_0$ may differ for different ablation applications targeting different tissues. These electric field strengths can typically be produced with an applied voltage in the range from approximately 1 kV to approximately 3 kV.

(iii) The pulse width $T_p$ is typically selected to be in the range between approximately 1 μs and approximately 10 μs to avoid significant heat generation and/or unwanted stimulation of muscle or nerve cells.

(iv) Substantially square pulses 922, 924 with a short rise time and a short fall time are preferred for therapeutic pulses to achieve an approximately maximum field strength for substantially entire pulse duration.

(v) Biphasic pulses 910 are delivered in trains of tens to hundreds pulses per train, for example, 50-200 pulses per train.

(vi) Pulse trains are typically delivered within a relatively short time interval, e.g., shorter than 200 ms, to fit into the refractory period of the surrounding myocardium. The inter-pulse delay is adjusted to achieve a desired train duration.

(vii) Therapeutic pulses are vectored between electrodes that are selected to produce a therapeutic electric field strength into the targeted volume of tissue. In different examples, such electrodes can be on a same catheter, on multiple catheters, or among catheter and surface/patch electrodes.

In some examples, one or more of the following considerations are applied when configuring the non-therapeutic waveform generator 142 for delivery of non-therapeutic waveforms:

(a) Biphasic waveforms, such as the waveform 902, may be preferred for the above-indicated reasons.

(b) The value of $\alpha V_0$ is selected to produce an electric field strength below the irreversible electroporation threshold. These electric field strengths can typically be produced with an applied voltage in the range from approximately 50 V to approximately 500 V.

(c) The pulse width $T_p$ is typically selected to be in the range between approximately 1 μs and approximately 50 μs to avoid stimulation of muscle or nerve cells. Heat is not an issue at low voltages. A variable pulse width $T_p$ to match or approximate the intended therapeutic dose(s) typically provides a more realistic picture of frequency dependent variables, such as the impedance.

(d) In various examples, non-therapeutic waveforms include square or rectangular waves, sine waves, triangular peak waves, multistep waves, or general single-phase waveforms. As such, the waveform 902 shown in FIG. 9 provides just one non-limiting example. Also, non-therapeutic waveforms do not have to be "biphasic" even though the biphasic feature confers the above-mentioned charge balancing benefits.

(e) Interelectrode deliveries may be at a relatively high frequency, e.g., to be completed in less than 200 ms or in approximately the same time duration as the corresponding therapeutic waveforms.

(f) In some examples, a single pulse is applied to each electrode with all other electrodes acting as a return path, followed by a second electrode and so-on, such that each individual electrode is powered with all others acting as return paths. Single pulses are typically considered to be a preferred embodiment as they consume less energy and time. In some other examples, pulse routines making use of multiple pulses may benefit from improved accuracy of the local measurement, provided that the entirety of such multiple pulses remains non-therapeutic.

(g) Electrodes to be evaluated for individual impedances may be preselected by the operator based on positioning within the anatomy as determined by the imaging and navigation system.

(h) Impedances between catheter electrodes and various surface electrodes may be evaluated to determine if some sets of electrodes can be configured to appropriately steer or direct the therapeutic delivery field.

(i) The inter-pulse delay may be selected to be as short as possible for non-therapeutic waveforms since heat generation is typically not an issue.

According to one example disclosed above, e.g., in the summary section and/or in reference to any one or any combination of some or all of FIGS. 1-9, provided is a medical-treatment apparatus, comprising: a plurality of electrodes placeable to be in electrical communication with a targeted site of a patient body; a waveform generator configured to selectively apply pulsed electrical waveforms to the plurality of electrodes; and an electronic controller configured to: estimate impedances of electrical paths in the patient body between an anchor electrode and a corresponding set of counter electrodes by causing the waveform generator to apply first waveforms thereto and sensing corresponding electrical currents, the anchor electrode and the corresponding set of counter electrodes being variously selected from the plurality of electrodes, the first waveforms being non-therapeutic waveforms; and select, based on the impedances, a group of electrodes for application of second waveforms to the targeted site, the group of electrodes including one or more of the variously selected anchor electrodes, the second waveforms being therapeutic waveforms.

In some examples of the above medical-treatment apparatus, the electronic controller is configured to cause the waveform generator to selectively apply the second waveforms to the group of electrodes.

In some examples of any of the above medical-treatment apparatus, the medical-treatment apparatus further comprises a first catheter, wherein the plurality electrodes includes a first array of electrodes located in a distal portion of the first catheter.

In some examples of any of the above medical-treatment apparatus, the medical-treatment apparatus further comprises a second catheter, wherein the plurality electrodes includes a second array of electrodes located in a distal portion of the second catheter.

In some examples of the above medical-treatment apparatus, the plurality electrodes includes one or more surface patch electrodes placeable on a skin of the patient body.

In some examples of the above medical-treatment apparatus, the electrical paths include one or more of: an electrical path between one electrode of the first array and another electrode of the first array; an electrical path between an electrode of the first array and an electrode of the second array; an electrical path between an electrode of the first array and one of the surface patch electrodes; and an electrical path between an electrode of the second array and one of the surface patch electrodes.

In some examples of the above medical-treatment apparatus, the first waveforms are selected from the waveform group consisting of: a biphasic waveform; a single-phase waveform; a rectangular-pulse wave; a sine wave; a triangular peak wave; and a multistep wave.

In some examples of the above medical-treatment apparatus, the second waveforms are biphasic rectangular-pulse waveforms.

In some examples of any of the above medical-treatment apparatus, the medical-treatment apparatus further comprises a mapping and navigation system configured to track positions of one or more of the plurality of electrodes to determine one or more distances between the anchor electrode and the corresponding set of counter electrodes.

In some examples of the above medical-treatment apparatus, the electronic controller is configured to estimate electric field strengths at the targeted site based on the one or more distances.

In some examples of the above medical-treatment apparatus, the electronic controller is configured to estimate pulsed-electric-field effects within the targeted site for the second waveforms based on the one or more distances.

In some examples of the above medical-treatment apparatus, the electronic controller is configured to generate a graphic image displaying an anatomical map of the targeted site having overlayed thereon the estimated pulsed-electric-field effects.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope the invention, which is limited only by the following claims.

What is claimed is:

1. A medical-treatment apparatus, comprising:
a plurality of electrodes placeable to be in electrical communication with a targeted site of a patient body;
a waveform generator configured to selectively apply pulsed electrical waveforms to the plurality of electrodes;
a mapping and navigation system configured to track positions of one or more of the plurality of electrodes to determine one or more distances between an anchor electrode and a corresponding set of counter electrodes; and
an electronic controller configured to:
estimate impedances of electrical paths in the patient body between the anchor electrode and the corresponding set of counter electrodes by causing the waveform generator to apply first waveforms thereto and sensing corresponding electrical currents, the anchor electrode and the corresponding set of counter electrodes being variously selected from the plurality of electrodes, the first waveforms being non-therapeutic waveforms;
select, based on the impedances, a group of electrodes for application of second waveforms to the targeted site, the group of electrodes including one or more of the variously selected anchor electrodes, the second waveforms being therapeutic waveforms; and
estimate pulsed-electric-field effects within the targeted site for the second waveforms based on the one or more distances.

2. The medical-treatment apparatus of claim 1, wherein the electronic controller is configured to cause the waveform generator to selectively apply the second waveforms to the group of electrodes.

3. The medical-treatment apparatus of claim 1, further comprising a first catheter,
wherein the plurality electrodes includes a first array of electrodes located in a distal portion of the first catheter.

4. The medical-treatment apparatus of claim 3, further comprising a second catheter,
wherein the plurality electrodes includes a second array of electrodes located in a distal portion of the second catheter.

5. The medical-treatment apparatus of claim 4, wherein the plurality electrodes includes one or more surface patch electrodes placeable on a skin of the patient body.

6. The medical-treatment apparatus of claim 5, wherein the electrical paths include one or more of:
an electrical path between one electrode of the first array and another electrode of the first array;
an electrical path between an electrode of the first array and an electrode of the second array;
an electrical path between an electrode of the first array and one of the surface patch electrodes; and
an electrical path between an electrode of the second array and one of the surface patch electrodes.

7. The medical-treatment apparatus of claim 1, wherein the first waveforms are selected from the waveform group consisting of:
a biphasic waveform;
a single-phase waveform;
a rectangular-pulse wave;
a sine wave;
a triangular peak wave; and
a multistep wave.

8. The medical-treatment apparatus of claim 7, wherein the second waveforms are biphasic rectangular-pulse waveforms.

9. The medical-treatment apparatus of claim 1, wherein the electronic controller is configured to generate a graphic image displaying an anatomical map of the targeted site having overlayed thereon the estimated pulsed-electric-field effects.

10. A medical-treatment method, comprising:

with a waveform generator, selectively applying pulsed electrical waveforms to a plurality of electrodes placed to be in electrical communication with a targeted site of a patient body;

with an electronic controller, estimating impedances of electrical paths in the patient body between an anchor electrode and a corresponding set of counter electrodes by applying first waveforms thereto and sensing corresponding electrical currents, the anchor electrode and the corresponding set of counter electrodes being variously selected from the plurality of electrodes, the first waveforms being non-therapeutic waveforms; and selecting, with the electronic controller and based on the impedances, a group of electrodes for application of second waveforms to the targeted site, the group of electrodes including one or more of the variously selected anchor electrodes, the second waveforms being therapeutic waveforms;

with a mapping and navigation system, tracking positions of one or more of the plurality of electrodes to determine one or more distances between the anchor electrode and the corresponding set of counter electrodes; and with the electronic controller, estimating pulsed-electric-field effects within the targeted site for the second waveforms based on the one or more distances.

11. The medical-treatment method of claim 10, further comprising:

with the electronic controller, causing the waveform generator to selectively apply the second waveforms to the group of electrodes.

12. The medical-treatment method of claim 10, wherein the plurality electrodes includes:

a first array of electrodes located in a distal portion of a first catheter;

a second array of electrodes located in a distal portion of a second catheter; and one or more surface patch electrodes on a skin of the patient body.

13. The medical-treatment method of claim 12, wherein the electrical paths include one or more of:

an electrical path between one electrode of the first array and another electrode of the first array;

an electrical path between an electrode of the first array and an electrode of the second array;

an electrical path between an electrode of the first array and one of the surface patch electrodes; and an electrical path between an electrode of the second array and one of the surface patch electrodes.

14. The medical-treatment method of claim 10, further comprising:

with the electronic controller, generating a graphic image displaying an anatomical map of the targeted site having overlayed thereon the estimated pulsed-electric-field effects.

15. A non-transitory computer-readable medium storing instructions that, when executed by an electronic controller of a medical-treatment apparatus, cause the medical-treatment apparatus to perform operations comprising the method of claim 10.

16. A medical-treatment apparatus, comprising:

a plurality of electrodes placeable to be in electrical communication with a targeted site of a patient body;

a waveform generator configured to selectively apply pulsed electrical waveforms to the plurality of electrodes;

a mapping and navigation system configured to track positions of one or more of the plurality of electrodes to determine one or more distances between an anchor electrode and a corresponding set of counter electrodes; and an electronic controller configured to:

estimate impedances of electrical paths in the patient body between the anchor electrode and the corresponding set of counter electrodes by causing the waveform generator to apply first waveforms thereto and sensing corresponding electrical currents, the anchor electrode and the corresponding set of counter electrodes being variously selected from the plurality of electrodes, the first waveforms being non-therapeutic waveforms;

select, based on the impedances, a group of electrodes for application of second waveforms to the targeted site, the group of electrodes including one or more of the variously selected anchor electrodes, the second waveforms being therapeutic waveforms; and estimate electric field strengths at the targeted site based on the one or more distances.

* * * * *